(12) United States Patent
Connelly et al.

(10) Patent No.: US 6,795,730 B2
(45) Date of Patent: Sep. 21, 2004

(54) MRI-RESISTANT IMPLANTABLE DEVICE

(75) Inventors: Patrick R. Connelly, Rochester, NY (US); Michael Weiner, West Henrietta, NY (US); Wilson Greatbatch, Akron, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 0 days.

(21) Appl. No.: 09/839,286

(22) Filed: Apr. 20, 2001

(65) Prior Publication Data

US 2002/0038135 A1 Mar. 28, 2002

Related U.S. Application Data

(60) Provisional application No. 60/198,631, filed on Apr. 20, 2000.

(51) Int. Cl.[7] ................................................. A61N 1/36
(52) U.S. Cl. ............................................. 607/9; 607/2
(58) Field of Search .............................. 607/4, 5, 9, 1, 607/2, 63, 64; 600/411, 413

(56) References Cited

U.S. PATENT DOCUMENTS

| | | |
|---|---|---|
| 4,091,818 A | 5/1978 | Brownlee et al. |
| 4,763,075 A | 8/1988 | Weigert |
| 5,089,697 A | 2/1992 | Prohaska |
| 5,217,010 A * | 6/1993 | Tsitlik et al. .................. 607/9 |
| 5,454,837 A | 10/1995 | Lindegren et al. |
| 5,520,190 A | 5/1996 | Benedict et al. |
| 5,601,611 A | 2/1997 | Fayram et al. |
| 5,649,965 A | 7/1997 | Pons et al. |
| 5,653,735 A | 8/1997 | Chen et al. |
| 5,776,167 A | 7/1998 | Levine et al. |
| 5,814,091 A | 9/1998 | Dahlberg et al. |
| 5,867,361 A | 2/1999 | Wolf et al. |
| 5,870,272 A | 2/1999 | Seifried et al. |
| 5,882,305 A | 3/1999 | Dumoulin et al. |
| 5,902,326 A | 5/1999 | Lessar et al. |
| 5,916,237 A | 6/1999 | Schu |
| 5,928,570 A | 7/1999 | Reo |
| 5,940,554 A | 8/1999 | Chang et al. |
| 5,946,086 A | 8/1999 | Bruce |
| 5,963,034 A | 10/1999 | Mahapatra et al. |
| 5,968,083 A | 10/1999 | Ciciarelli et al. |
| 5,987,995 A | 11/1999 | Sawatari et al. |
| 6,005,191 A | 12/1999 | Tzeng et al. |
| 6,013,376 A | 1/2000 | Yenni, Jr. |
| 6,016,448 A | 1/2000 | Busacker et al. |
| 6,023,641 A | 2/2000 | Thompson |
| 6,029,086 A | 2/2000 | Kim et al. |
| 6,029,087 A | 2/2000 | Wohlgemuth |
| 6,031,710 A | 2/2000 | Wolf et al. |
| 6,044,301 A | 3/2000 | Hartlaub et al. |

(List continued on next page.)

OTHER PUBLICATIONS

*Taking advantage of Sophisticated Pacemaker Diagnostics*, Bernd Nowak, MD, in Symposim: Electrical Management of Cardiac Disorders, pp. 172D–179D, American Journal of Cardiology vol. 83, Excerpta Medical Inc., Mar. 11, 1999.

(List continued on next page.)

*Primary Examiner*—George R. Evanisko
(74) *Attorney, Agent, or Firm*—Kenyon & Kenyon

(57) ABSTRACT

An implantable device used to monitor and maintain at least one physiologic function, which is capable of operating in the presence of damaging electromagnetic interference. The implantable device includes primary and secondary modules, each independently protected from EMI damage via at least one shielding and/or filtering, and a non-electrical communication device for communicating in at least one direction between the primary and the secondary modules. The primary module, in response to input from electrical sensing leads, activates the secondary module in a failsafe mode. In the failsafe mode, the secondary module carries out a physiologic function upon activation and in the presence of electromagnetic interference.

10 Claims, 4 Drawing Sheets

U.S. PATENT DOCUMENTS

| | | | |
|---|---|---|---|
| 6,052,623 | A | 4/2000 | Fenner et al. |
| 6,055,455 | A | 4/2000 | O'Phelan et al. |
| 6,067,472 | A | 5/2000 | Vonk et al. |
| 6,080,829 | A | 6/2000 | Tapsak et al. |
| 6,090,473 | A | 7/2000 | Yoshikawa et al. |
| 6,090,728 | A | 7/2000 | Yenni, Jr. et al. |
| 6,091,744 | A | 7/2000 | Sorin et al. |
| 6,091,987 | A | 7/2000 | Thompson |
| 6,101,973 | A | 8/2000 | Stewart et al. |
| 6,118,910 | A | 9/2000 | Chang |
| 6,119,031 | A | 9/2000 | Crowley |
| 6,142,678 | A | 11/2000 | Cheng |
| 6,144,866 | A | 11/2000 | Miesel et al. |
| 6,188,926 | B1 | 2/2001 | Vock |
| 6,192,261 | B1 | 2/2001 | Gratton et al. |

OTHER PUBLICATIONS

*Interaction of a Commercial Heart Rate Monitor With Implanted Pacemakers*, Jose A. Jaglar, MD, et al., pp. 790–792, Brief Reports, American Journal of Cardiology vol. 83, Excerpta Medical Inc., Mar. 11, 1999.

*Electromagnetic interference shielding using continuous carbon–fiber carbon–matrix and polymer–matrix composites*, Xiangcheng Luo, D.D.L. Chung, in Composites: Part B 30, pp. 227–231, Elsevier Sciences Ltd. (1999).

*Polypyrrole–based conducting hot melt adhesives for EMI shielding applications*, J.A. Pomposo, et al., in Synthetic Metals 104, pp. 107–111, Elsevier Sciences Ltd. (1999).

*Fiber optic sensor technology: an overview*, K.T.V. Grattan, et al., in Sensors and Actuators 82, pp. 40–61, Elsevier Sciences Ltd. (2000).

*Optical and acoustic damage detection in laminated CFRP composite materials*, L. Rippert, et al., in Composites Science and Technology 60, pp. 2713–2724, Elsevier Sciences Ltd. (2000).

*A production process of silicon sensor elements for a fibre–optic pressure sensor*, Carola Strandman, et al., in Sensors and Actuators 63, pp. 69–74, Elsevier Sciences Ltd. (1997).

*A single–fringe etalon silicon pressure transducer*, D.L. Howard, et al., in Sensors and Actuators 86, pp. 21–25, Elsevier Sciences Ltd. (2000).

*Displacement sensing using geometrical modulatin in reflection mode (GM–RM) of coupled optical waveguides*, Dan Haronian, in Journal of Micromech. Microeng. 8, pp. 323–326, IOP Publishing (1998) (UK).

*A novel distributed feedback laser diode structure for an optical wavelength tunable filter*, H. Ghafouri–Shiraz, et al., in Semiconductor Science and Technology 12, pp. 1161–1165, IOP Publishing (1997) (UK).

*A new optical fibermultiplexer for distortion–free light transfer in multichannel fiber optic sensor systems*, Larissa Kasarian, et al., in Sensors and Actuators 84, pp. 250–258, Elsevier Sciences Ltd. (2000).

*Electric–field–controlled 2×2 bypass–exchange photorefractive switch*, Xiaona Yan, et al., in Journal of Optics 29, pp. 383–386, IOP Publishing (1998) (UK).

*A micromachined vibration sensor based on the control of power transmitted between optical fibres*, E. Peiner, et al., in Sensors and Actuators 65, pp. 23–29, Elsevier Sciences Ltd. (1998).

*High–performance unidirectional electrooptic modulator based on polymeric highly multi–mode waveguides*, David Sun, et al., in Optics and Laser Technology 30, pp. 481–489, Elsevier Sciences Ltd. (1998).

*Microchip lasers and their applicationos in optical microsystems*, Engin Molva, in Optical Materials 11, pp. 289–299, Elsevier Sciences Ltd. (1999).

*Theory and design of an integrated optical sensor based on planar waveguiding lenses*, Jesus Linares, et al., in Optics Communications 180, pp. 29–36, Elsevier Sciences Ltd. (2000).

*Coupling gratings as waveguide functional elements*, Olivier Parriaux, et al., in Pure and Applied Optics 5, pp. 453–469, IOP Publishing (1996) (UK).

*Three–dimensional microfabrication for a multi–degree–of–freedom capacitive force sensor using fibre–chip coupling*, E T Enikov, et al., in Journal of Micromech. Microeng. 10, pp. 492–497, IOP Publishing (2000) (UK).

*Through–etched silicon carriers for passive alignment of optical fibers to surface–active optoelectronic components*, Johan Holm, et al., in Sensors and Actuators 82, pp. 245–248, Elsevier Sciences Ltd. (2000).

*Vibration sensor using optical–fiber cantilever with bulb–lens*, Mitsuteru Kimura, et al., in Sensors and Actuators 66, pp. 178–183, Elsevier Sciences Ltd. (1998).

*Three–stage wavelength converter based on cross–gain modulation in semiconductor optical amplifiers*, Y. Mao, et al., in Optics Communications 167, pp. 57–66, Elsevier Sciences Ltd. (1999).

*Dynamically induced irreversibility: light amplification and quantum noise reduction in a V–type three–level system*, Xiang–ming Hu, et al., in J. Opt. B: Quantum Semiclass. Opt. 2, pp. 570–575, IOP Publishing (2000) (UK).

*Lithium niobate integrated–optic voltage sensor with variable sensing ranges*, Yong–Sik Yim, et al., Optics Communications 152, pp. 225–228, Elsevier Sciences Ltd. (1998).

*Electromagnetic interference shielding efficiency of polyaniline mixtures and mulitilayer films*, C. Y. Lee, et al., in Synthetic Metals 102, pp. 1346–1349, Elsevier Sciences Ltd. (1999).

*Optoelectronics–VLSI system integration Technological challenges*, Marc P.Y. Desmulliez, in Materials Science and Engineering, pp. 269–275, Elsevier Sciences Ltd. (2000).

*Fiber–optic vibration sensor based on frequency modulation of light–excited oscillators*, J. David Zook, et al., in Sensors and Actuators 83, pp. 270–276, Elsevier Sciences Ltd. (2000).

*Attenuation of low frequency magnetic fields using active shielding*, Manuel Reta–Hernandez, et al., in Electric Power Systems 45 (1998), pp. 57–63, Elsevier Sciences Ltd. (1998).

*The EMI shielding effectiveness of PC/ABS/nickel–coated–carbon–fibre composites*, Chi–Yuan Huang, et al., in European Polymer Journal 36, pp. 2729–2737, Elsevier Sciences Ltd. (2000).

*Flexible Graphite for Gasketing, Adsorption, Electromagnetic Interference Shielding, Vibration Damping, Electyrochemical Applications, and Stress Sensing*, D.D.L. Chung, in Journal of Materials Engineering and Performance 9, pp. 161–163, ASM International (2000).

*Optical link for digital transmissions using porous silicon light emitting diode*, M. Balucani, et al., in Journal of Non–Crystalline Solids 266–269, pp. 1238–1240, Elsevier Sciences Ltd. (2000).

\* cited by examiner

MRI-RESISTANT IMPLANTABLE DEVICE

PRIOR PROVISIONAL APPLICATION

This application claims the benefit under 35 U.S.C. § 119(e) of U.S. Provisional Patent Application Ser. No. 60/198,631, filed on Apr. 20, 2000.

FIELD OF THE INVENTION

The present invention relates to an MRI-resistant implantable device. The implantable device of the present invention permits satisfactory performance in the presence of the electromagnetic fields emanated during magnetic resonance imaging (MRI) procedures. Patients provided with the present invention can undergo MRI procedures, and gain the benefits therefrom, while maintaining the use of the diagnostic and therapeutic functions of the implantable device.

BACKGROUND INFORMATION

Implantable devices such as implantable pulse generators (IPGs) and cardioverter/defibrillator/pacemaker (CDPs) are sensitive to a variety of forms of electromagnetic interference (EMI). These devices include sensing and logic systems that respond to low level signals from the heart. Because the sensing systems and conductive elements of these implantable devices are responsive to changes in local electromagnetic fields, they are vulnerable to external sources of severe electromagnetic noise, and in particular to electromagnetic fields emitted during magnetic resonance imaging (MRI) procedures. Therefore, patients with implantable devices are generally advised not to undergo MRI procedures.

With the exception of x-ray procedures, MRI procedures are the most widely applied medical imaging modality. Significant advances occur daily in the MRI field, expanding the potential for an even broader usage. There are primarily three sources of energy that could lead to the malfunction of an implantable device, during an MRI procedure. First, a static magnetic field is generally applied across the entire patient to align proton spins. Static magnetic field strengths up to 7 Tesla for whole body human imaging are now in use for research purposes. The increase in field strength is directly proportional to the acquired signal to noise ratio (SNR) which results in enhanced MRI image resolution. Consequently, there is impetus to increase static field strengths, but with caution for patient safety. These higher field strengths are to be considered in the development of implantable devices.

Second, for image acquisition and determination of spatial coordinates, time-varying gradient magnetic fields of minimal strength are applied in comparison to the static field. The effects of the gradients are seen in their cycling of direction and polarity. With present day pulse sequence design and advances in MRI hardware, it is not uncommon to reach magnetic gradient switching speeds of up to 50 Tesla/sec (this is for clinical procedures being used presently). Additionally, fast imaging techniques such as echo-planar imaging (EPI) and turbo FLASH are in use more frequently in the clinic. Non-invasive magnetic resonance angiography uses rapid techniques almost exclusively on patients with cardiovascular disease. Previous research evaluating the effects of MRI on pacemaker function did not include these fast techniques. Therefore, the use of MRI for clinical evaluation for individuals with implantable cardiac devices may be an issue of even greater significance. Rapid MRI imaging techniques use ultra-fast gradient magnetic fields. The polarities of these fields are switched at very high frequencies. This switching may damage implantable devices or cause them to malfunction.

Lastly, a pulsed RF field is applied for spatial selection of the aligned spins in a specimen during an MRI procedure. FDA regulations relative to the power limits of the RF fields are in terms of a specific absorption rate (SAR), which is generally expressed in units of watts per kilogram. These limits may not consider the effects on implantable devices as the deleterious effects of transmission of RF fields in the MRI system may no longer be the primary concern in their design parameters.

While advancements in techniques used to protect implantable devices from MRI fields have been made, the techniques described mainly concern incorporating additional protective circuitry in the implantable devices or providing alternative modes of operation in response to electromagnetic insult. For example, U.S. Pat. No. 5,217,010 to Tsitlik et al. describes the use of inductive and capacitive filter elements to protect internal circuitry; U.S. Pat. No. 5,968,083 to Ciciarelli et al. describes switching between low and high impedance modes of operation in response to EMI insult; and U.S. Pat. No. 6,188,926 to Vock concerns a control unit for adjusting a cardiac pacing rate of a pacing unit to an interference backup rate when heart activity cannot be sensed due to EMI.

However, the techniques described do not provide a fail-safe system in the case that the protective circuitry or the alternative modes of the implantable device fails to protect the implantable device from malfunction due to exposure to electromagnetic fields. What is needed is a modular backup system that is resistant to electromagnetic insult and can support the basic functionality of the implantable device, so that if the device fails to function for a duration, such as during an MRI procedure, the backup system can provide the necessary assistance functions.

SUMMARY OF THE INVENTION

The present invention provides an implantable device that is resistant to electromagnetic interference comprising first and second modules and a non-optical arrangement for communication between the first module and the second module. During a normal operating mode the first module performs physiologic functions and the second module is deactivated. When electromagnetic interference is detected, the second module, which is resistant to EMI insult, is activated and the first module is deactivated to further protect its components from EMI.

The present invention also provides an implantable device used to monitor and maintain at least one physiologic function, which is capable of operating in the presence of damaging electromagnetic interference. The implantable device includes primary and secondary modules, each independently protected from EMI damage via at least one shielding and/or filtering, and a non-electrical communication device for communicating in at least one direction between the primary and the secondary modules. The primary module, in response to input from electrical sensing leads, activates the secondary module in a failsafe mode. In the failsafe mode, the secondary module carries out a physiologic function upon activation and in the presence of electromagnetic interference.

In an advantageous embodiment, the physiologic function performed by the implantable device is a cardiac assist function, and the implantable device is a cardiac assist device.

DETAILED DESCRIPTION

Figure 1:
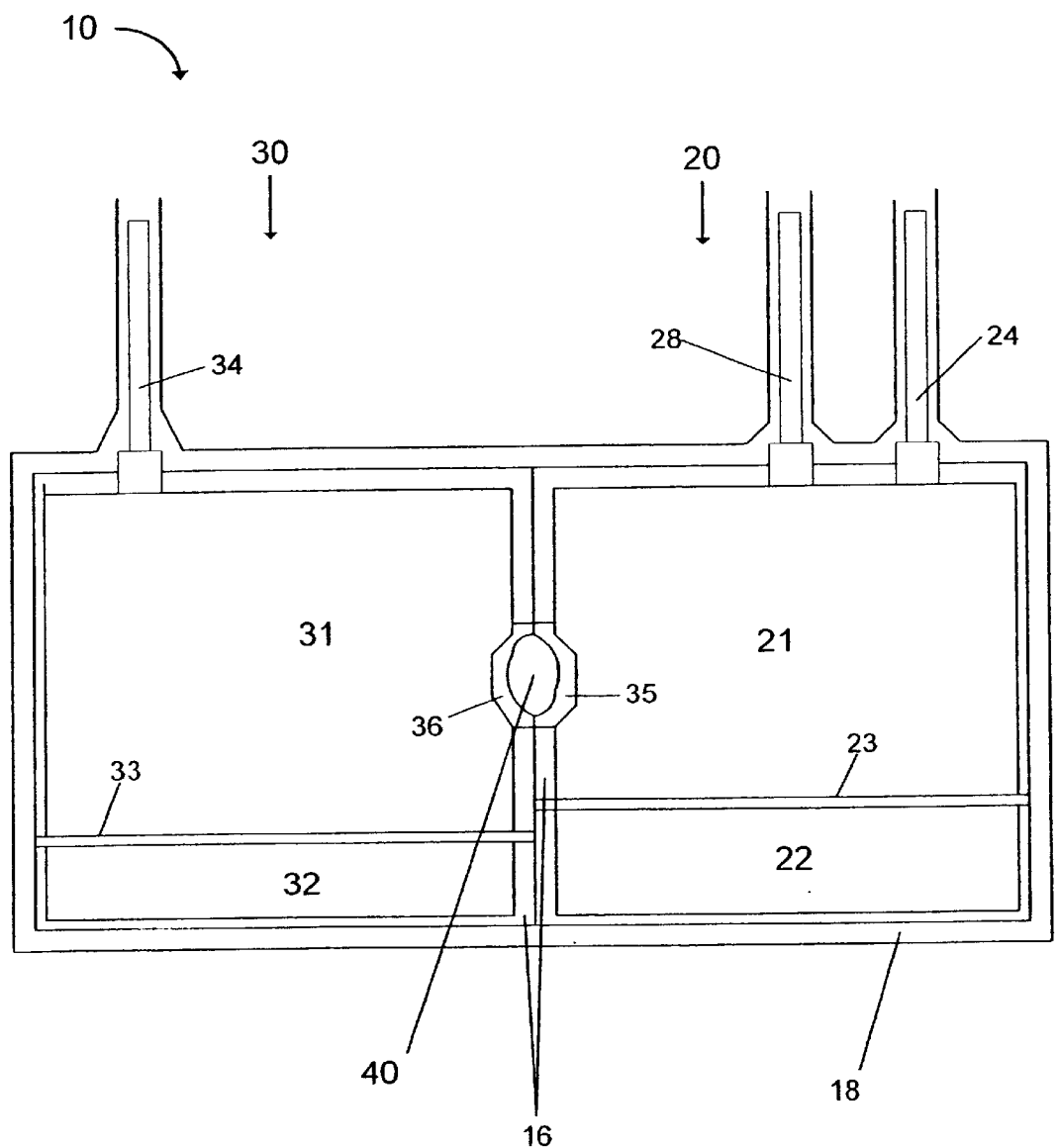
FIG. 1 shows a cross-section of an implantable device according to an embodiment of the present invention.

A cross-section diagram of an embodiment of the implantable device according to the present invention is shown in FIG. 1. The body of the device 10 is shown in rectangular form for illustrative purposes only and may have a rounded shape when implanted in the body to avoid tissue damage due to sharp edges. The body of the implantable device 10 includes two modules, a primary module 20 and a secondary module 30, which are hermetically sealed from each other. As will be described further below, according to an exemplary embodiment of the present invention, the primary module is a demand pacemaker (DDD) with PCD functionality. As is known in the art, a demand (DDD) pacemaker denotes an implantable device that paces and senses both atrial and ventricle chambers of the heart and can either trigger or inhibit functions depending on detected parameters. During normal operation, the secondary module 30 is deactivated, and the primary module 20 controls the various pacing, cardioversion and defibrillation operations of the implantable device 10 via electrical pacing lead 24. The primary module 20 also detects parameters indicating how the heart is functioning via electrical sensing lead 28. Both the pacing leads and sensing leads are bipolar leads.

The primary module 20 includes a circuitry portion 21 which contains signal detection and logic circuitry for performing pacing and analysis functions and a battery portion 22. The battery portion 22 includes either no magnetic material or non-magnetic materials. It may be, for example, a lithium-iodine battery, or its equivalent in another chemistry; e.g., it may have an anode of lithium or carbon and a cathode of iodine, carbon monofluoride, silver vanadium oxide, sulfur dioxide, $SOCl_2$, or $SO_2\ Cl_2$. The circuitry portion 21 is separated from the battery portion 22 by a non-magnetic and non-corrosive layer 23 which, as described below, can be made from titanium or from a carbon-composite material.

The implantable device 10 also includes a secondary module 30 which contains independent circuitry 31 and battery portion 32 also separated by a non-magnetic and non-corrosive layer 33. The secondary module 30 is not activated when the primary module 20 operates, but is only switched on when the primary module 20 malfunctions or detects a voltage induced by electromagnetic interference (EMI) that exceeds a certain level, such as, for example, 3 Volts. During such an occurrence, the secondary module 30 acts as a backup VOO pacemaker, which is ventricle driven, with no ventricle-sensing input nor any ventriculr triggering or inhibition. The secondary module 30 sends pacing signals via unipolar electrical lead 34 to a ventricle chamber of the heart but does not receive any detected input signals. In accordance with its backup function, the secondary module 30 is supplied with power by a separate battery 32, which is also of a non-magnetic type, such as a lithium-iodine battery or those other kinds discussed above.

Both the primary and secondary modules 20, 30 are encased within shieldings 16 that protect their respective circuitry components from external electromagnetic fields. The shieldings 16 can be made from carbon-matrix composites with continuous carbon fiber filler, which is particularly effective in EMI shielding, as discussed in *Electromagnetic interference shielding using continuous carbon-fiber carbon-matric and polymer-matrix componsites*, Luo, X., and Chung, D. D. L., in Composites: Part B (1999), and also suitable for injection molding to encase circuit components. The thickness of the shieldings 16 varies from approximately 1 to 3 millimeters. In addition, the batteries of the primary and secondary modules 22, 32 are also encased in separate shieldings 16 made of similar materials.

An optical window 40, made from glass or ceramic, which may be an infrared-transmissive window, is situated between the respective circuitry portions 21 and 31 of the primary and secondary modules 20, 30. The optical window 40 allows for communication to occur between the primary and secondary modules 20, 30. The window 40 is transparent to a range of frequencies of visible or infrared radiation. The thickness of the window has an optimal range of between 0.3 and 1 centimeter. To maintain a hermetic seal between the modules 20, 30, the optical window 40 is bound with brazing to sealing fixtures 35, 36 (also referred to as ferrules) that are welded to the shielding layers 16 of the respective modules 20, 30 in a manner that may correspond, for example to that described in, for example, U.S. Pat. No. 5,902,326 to Lessar et al.

To further protect the implantable device 10 from external electromagnetic fields, the entire implantable device 10, including the electrical leads 24, 28, 34, is coated with a non-magnetic, biocompatible layer 18 such as rolled titanium or flexible graphite. Flexible graphite has been shown to be a particularly effective shielding gasket material as discussed, for example, in *Flexible Graphite for Gasketing, Adsorption, Electromagnetic Interference Shielding, Vibration Damping, Electrochemical Applications, and Stress Sensing*, Chung, D. D. L., Journal of Mat. Eng. and Performance, Vol. 92 (2000), due to its resilience, chemical resistance, and shielding properties. Graphite/polymer composites may also serve as layer 18. With both the inner 16 and outer 18 shielding layers in place, only the ends of the electrical leads 24, 28, 34, that are in direct contact with heart tissue remain vulnerable to electromagnetic fields. Since the ends of the leads 24, 28, 34 must be exposed in order to pace the heart or detect electrical impulses, electromagnetic interference can propogate through the ends of the leads 24, 28, 34 to the circuitry of the primary and secondary modules 20, 30. The circuitry described below addresses this problem.

Figure 2:
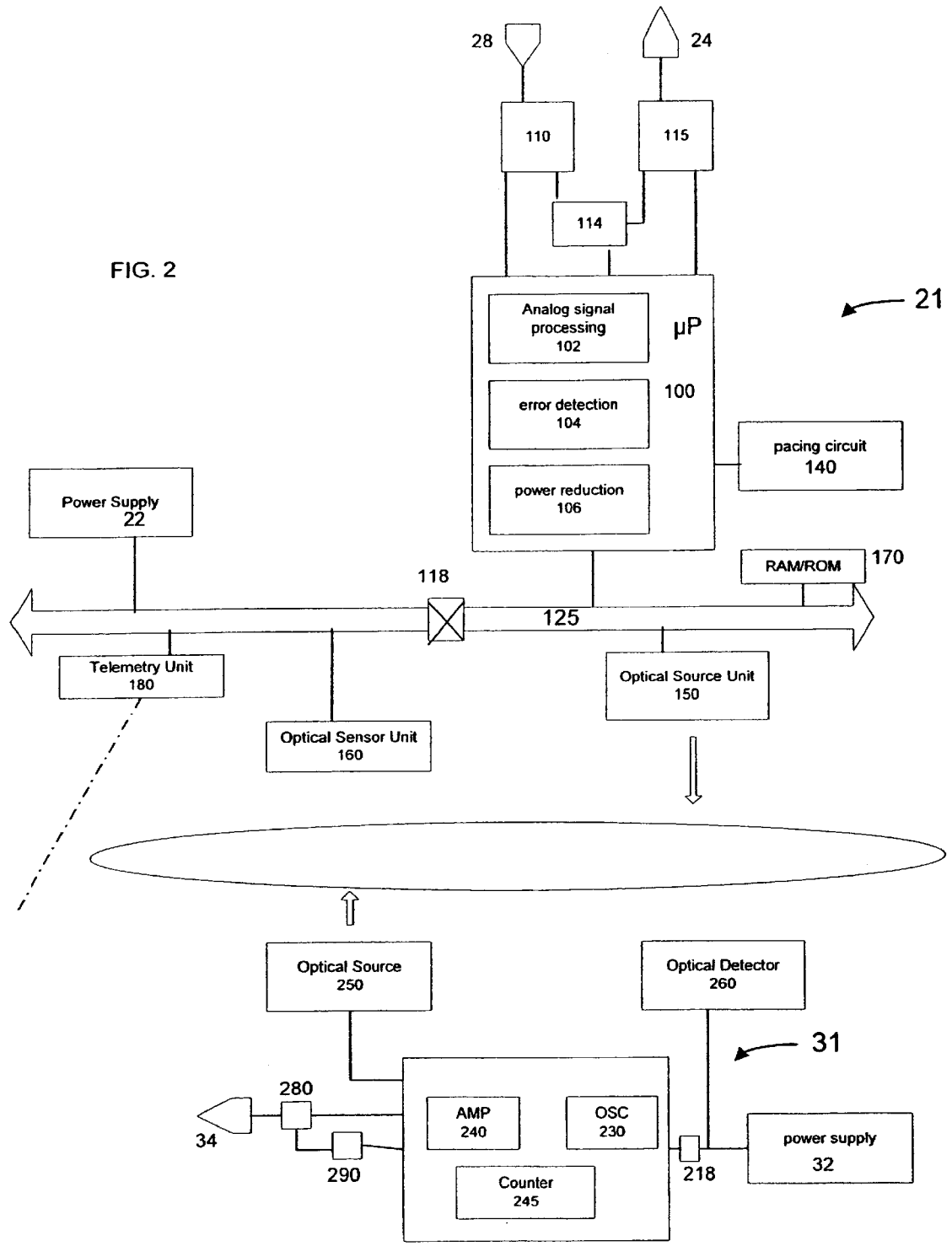
FIG. 2 is a block diagram showing functional components of an implantable device according to an embodiment of the present invention.

FIG. 2 shows functional components of a dual-module implantable device 10 according to an embodiment of the present invention. As shown, the functional components of the primary module 20 include a power supply (from the battery 22) which supplies power along a main power and device communication bus 125 to the circuitry 21. The circuitry 21 includes a processor 100 coupled to the main bus 125, which can be implemented as a parallel processor, or as a microprocessor adapted to perform analog signal processing functions 102 in addition to error detection 104 and power reduction operations 106. In the analog processing mode 102, the processor 100 analyzes cardiac signals input from the sensing lead 28 and determines a QRS complex from the various properties of the input signals.

The processor 100 determines from the analysis, in a manner know in the art, whether a detrimental heart condition exists, and directs a pacing circuit 140 to transmit corrective pulses to ameliorate the condition.

The processor 100 is also configured to detect internal errors or circuitry malfunctions. As will be described further, when such errors are detected, the processor 100, initiates a shut down of the primary module 20 and sends a signal via optical window 40 that instructs module 30 to become activated. Furthermore, to preserve the life of the battery 22 for as long as possible, the processor 100 regulates the application of power to various circuit elements in order to reduce static power consumption, in a manner such as described, for example, in U.S. Pat. No. 5,916,237 to Schu. The processor 100 is coupled to a memory unit 170 in which instructions and data are stored for performing the functions described herein.

The primary module circuitry 21 also includes an optical source unit 150 coupled to the main bus 125. Optical source unit 150 can be any source of visible or infrared radiation that does not consume significant amounts of power, such as a light emitting diode (LED). During normal operation of the primary module 20, the optical source 150, according to various implementations known in the art, turns on and off with a specific well-defined frequency or remains continually on. The optical source unit 150 is arranged in relation to the optical window 40 so that radiation emitted from the source unit 150 penetrates through the optical window 40 into the secondary module 30. Both the processor 100 and the optical source unit 150 are situated downstream from a power-down switch 118.

The primary module circuitry 21 also includes an optical sensor unit 160 similarly placed in relation to the optical window 40, in this case, so that it can receive radiation emitted from sources within the secondary module 30. The optical sensor unit 160 is a low-power photodetector sensitive to infrared or visible radiation of a certain frequency range. The optical sensor unit 160 is coupled to the main bus 125 upstream from the power-down switch 118, so that it remains connected to the power supply 22 via the main bus 125 and therefore remains functional, even when the power-down switch 118 is opened.

Similarly, a telemetry unit 180 is also situated upstream from the power-down switch 118 so it also can function when the power-down switch 118 is opened. The telemetry unit 180 may be, for example, any well known subcutaneous near-infrared signal transmitter, for example, such as described in U.S. Pat. No. 6,192,261 to Gratton et al., that radiates through body tissues and can communicate with a near-by remote programming device (not shown) equipped with an infrared receiver, for example, during an examination at a medical facility. In another implementation, the telemetry unit may use low-power high-frequency radio signals in the Bluetooth™ range to communicate with nearby Bluetooth™-enabled network devices. In either case, the telemetry unit 180 can communicate information such as the condition of the heart, the remaining life of the implantable device batteries, and whether the primary module 20 is inoperative.

The processor 100 is coupled to pacing lead 24 and sensing lead 28 via respective comparators 110 and 115. The comparator 110 compares voltage on the input lead 28 with a threshold voltage, set to, for example 3 Volts. If the input voltage exceeds the threshold voltage, the comparator 110 sends a signal to the processor 100. The comparator 115 is reverse biased, so that it compares voltages caused by external fields, rather than the output pulse signal on the pacing lead 24, to the threshold voltage, also set to, for example, 3 Volts. If the external voltage appearing on the pacing lead exceeds the threshold voltage, the comparator 115 sends a signal to the processor 100.

When a voltage exceeds the threshold, this indicates that external EMI fields, which may be caused by an MRI device, are present, and that normal operation of the primary module 20 is to cease. To protect the primary module 20 from excessive voltage signals, a switch (not shown) is thrown to redirect lead signal through capacitive and inductive elements 114, which filter signals on the pacing 24 and sensing 28 leads in a way known in the art before they reach the circuitry 21 of the primary module 20. Upon receiving from either comparators 110 or 115 a signal that the threshold voltage has been exceeded, the processor 100 sends a power-down signal to open the switch 118. Additionally, the processor 100 may send a power-down signal to open the switch 118 in response to detection of internal errors or malfunctions. U.S. Pat. No. 5,653,735 describes, for example, one way by which error detection module 104 can detect malfunctions in primary module 20 not caused by EMI.

When the power-down switch 118 is opened, the primary module circuitry components downstream from the switch are disconnected from the power supply 22 and no longer operate. In particular, the primary module 20 stops transmitting pacing pulses to the heart and the optical source unit 150 stops radiating through the optical window 40. As noted above, the telemetry unit 180 and the optical sensor unit 160 of the primary module 20 continue operating.

When the optical source unit 150 of the primary module 20 stops emitting radiation, this event is detected by the optical detector 260 of the secondary module 30, which is adapted to detect an absence of radiation of either a certain frequency or for a defined period of time, for example, two seconds. Upon detection, the optical detector 260 transmits a power-up signal to switch 218, which closes and connects the secondary module circuitry 31 to the secondary power supply 32. In this manner, the secondary module 30 is activated when the primary module 20 is deactivated.

Figure 3:
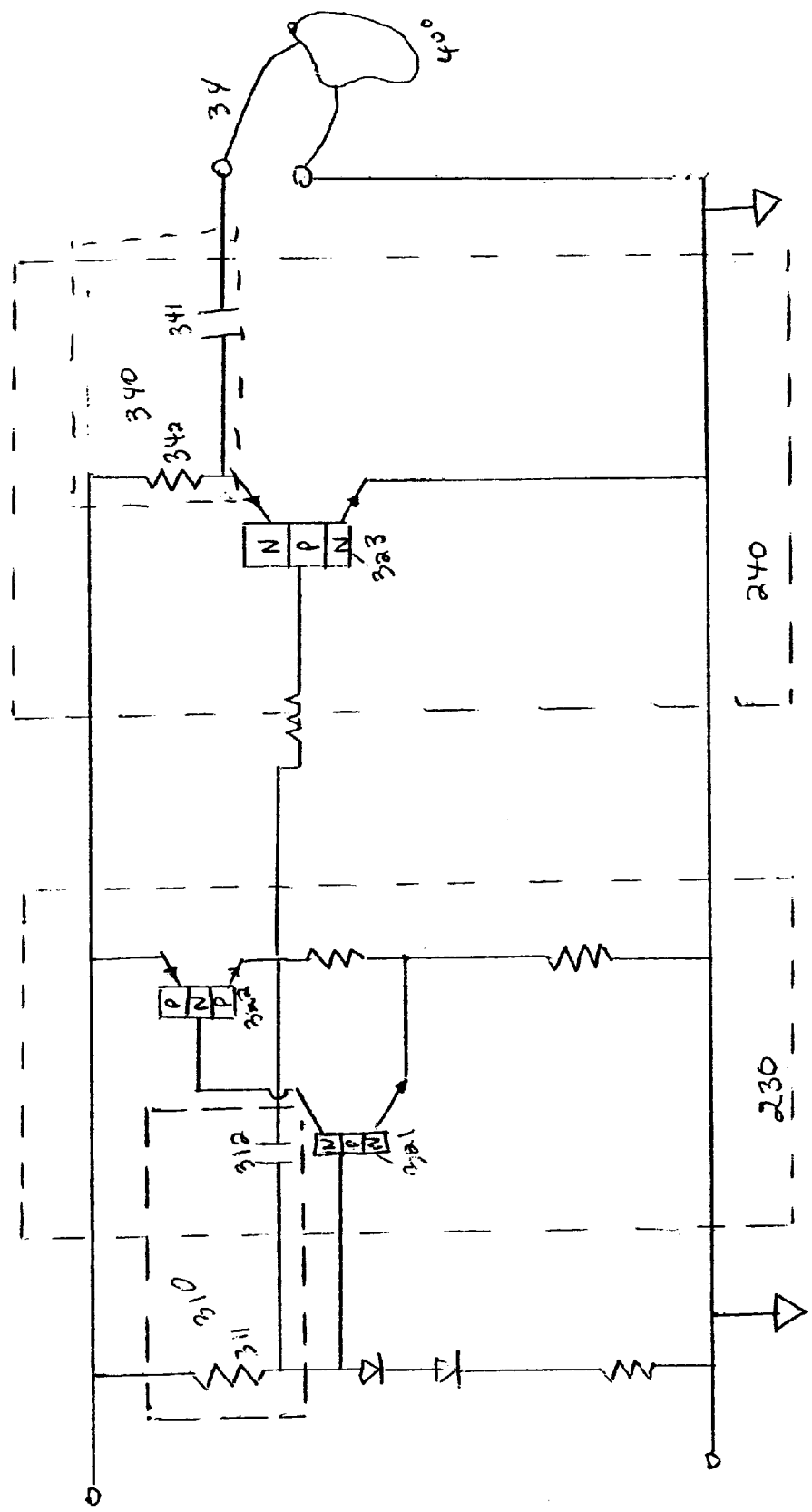
FIG. 3 shows an embodiment of the robust pacing circuitry included in the secondary module of the implantable device according to an embodiment of the present invention.

The secondary module circuitry 31 includes an oscillator stage 230, an amplifier stage 240 and a counter 245. FIG. 3 shows an exploded view of the oscillator 230 and amplifier 240 stages, which are comprised of robust electrical components, such as bipolar transistors, that are not easily disturbed by electromagnetic insult. The oscillator 230 includes bipolar transistors 321 and 322 which are coupled in an emitter feedback arrangement. The RC circuit 310 comprised of resistor 311 and capacitor 312 sets the fixed repetition rate of the oscillator 230. Once the secondary module 30 is turned on, a pulse is produced and sent on to an amplifier stage 240 comprising bipolar transistor 323. A shaping RC circuit 340, comprising capacitor 341 and resistor 342 modifies the shape of a pulse that triggers the ventricle tissues in the heart (shown as 400). This secondary module circuitry 31 generates an electrical pulse that stimulates the heart tissues via a lead 34 extending from the secondary module 30, whereby it produces ventricular contraction at a fixed rate. The return path for the pulse signal is through lead 34 from the heart 400 to the secondary module 30. Since the pacing lead 34 can conduct electromagnetic interference, a reverse biased comparator 280 switches the conducting path to capacitive and inductive filtering elements 290 when a threshold voltage is reached in a manner known in the art. The arrangement of comparator 280 and filtering elements 290 adds an extra layer of protection to the secondary module circuitry 31, but is not necessary to the operation of circuitry 31.

Because the secondary module 30 only performs basic pacing operations and does not perform diagnostic functions, if the primary module 20 shuts down in response to temporary electromagnetic interference, it is important to reactivate the primary module 20 (and deactivate the secondary module 30) when the implantable device 10 is no longer threatened by the electromagnetic interference. For example, since MRI procedures generally last approximately half an hour, the primary module 20 should only be deactivated for a half an hour plus an additional amount as a tolerance factor, for example.

To keep track of the length of time the secondary module 30 is operating, the secondary module circuitry 31 includes a counter element 245 coupled to the oscillator element 230, that counts oscillator transitions. Once the secondary module 30 is turned on, the counter element 245 increments and can trigger a reset function to turn the primary module 20 back on when it reaches a specific count after a pre-defined length of time. In one embodiment, the counter 245 triggers an optical source 250 to transmit radiation through the optical window 40 to the primary module 20 in which the radiation is detected by optical sensor unit 160. For example, this radiation may be a single pulse lasting for one second. In response to detection of radiation, the optical sensor unit 160 sends a trigger signal to close the power-down switch 118 and turn the primary module 20 back on. When the processor 100 of the primary module 20 detects that it is connected to the power supply 22, it runs diagnostic tests in a power-on-reset (POR) mode, such as described, for example, in U.S. Pat. No. 6,016,448 to Busacker et al., wherein initial conditions of the heart are determined and stored in memory unit 170. During this mode, the processor 100 also runs internal error checks, so that if the original power-down was caused by internal malfunction, and the cause of the malfunction has not been corrected, the secondary module 30 is not deactivated.

If the internal error checks indicate that the primary module circuitry 21 can support the PCD cardiac assist functions properly, the processor 100 sends a trigger to the pacing unit 140 to begin operation and simultaneously sends a transmission signal to the optical source unit 150, whereupon the optical source unit 150 turns on or begins to pulse according to its pre-set frequency. The optical detector 260 of the secondary unit then detects that the optical source unit 150 of the primary unit is on, and in response, triggers the switch 218 to open, deactivating the secondary module circuitry 31.

Figure 4:
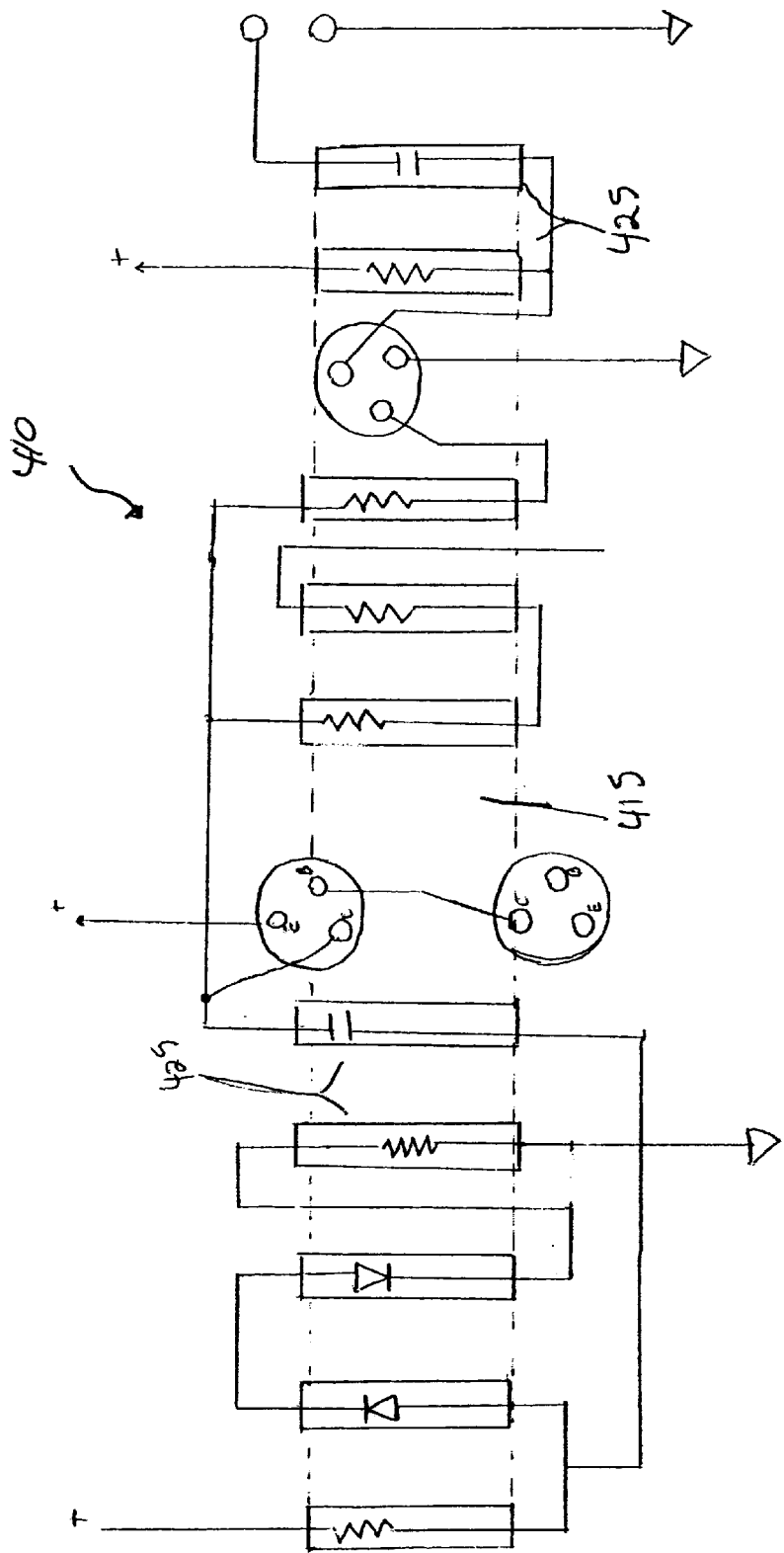
FIG. 4 represents a "cordwood" construction embodiment of the pacing circuitry of the secondary module according to the present invention.

To further improve the EMI resistance of the secondary module 30, the circuitry components 31 may be arranged, according to one embodiment of the secondary module circuitry 31, in a "cordwood" design such as is shown in FIG. 4. As illustrated, in this arrangement all components are laid side by side on a teflon block 415, to avoid adherence, and a thin layer of mixed epoxy is laid onto the circuit components, which are aligned so as to minimize the wiring between the various components which reduces extraneous induced EMI pickup. When the epoxy has cured, the circuit 410 is removed from the teflon block and the components are wired as illustrated in FIG. 4. The resistor and capacitor components 425 are shown hand-wired with very short leads, which reduces electrical pickup signals from an MRI in progress that might disturb the operation of the pacemaker circuitry.

In a second embodiment, the secondary module circuitry 31 comprises a custom designed integrated circuit (IC) fabricated, with the active semiconductors, resistors, capacitors and the connecting wires part of the IC. Generally speaking, a monolithic IC of this type maybe exemplified in a manner similar to that described, for example, in U.S. Pat. No. 5,649,965 to Pons et al.

While there has been described and pointed out the fundamental novel features of the invention as applied to the preferred embodiments, it will be understood that various omissions and substitutions and changes in the form and details of the devices illustrated, as well as its operation, may be made by those skilled in the art, without departing from the spirit of the invention.

What is claimed is:

1. An implantable capable of operating in the presence fan electromagnetic interference, comprising:

a primary module configured to operate in a normal operating mode in the absence of the electromagnetic interference;

a secondary module, each one of the primary module and the secondary module being independently protected from damage due to the electromagnetic interference via at least one of a shielding and a filtering;

a sensing lead coupled to the primary module; and a non-electrical communication device for communicating in at least one direction between the primary module and the secondary module, wherein the primary module, in response to an input from the sensing lead, activates, via the non-electrical communication device, the secondary module to operate in a failsafe mode, and wherein the secondary module carries out at least one physiologic function upon activation and in the presence of the electromagnetic interference.

2. An implantable device as in claim 1, wherein the implantable device returns to the normal operating mode from the failsafe mode upon a cessation of the electromagnetic interference.

3. An implantable device as in claim 1, wherein the shielding includes one of a non-magnetic metal, carbon, a carbon composite, and a combination thereof.

4. An implantable device as in claim 1, wherein the primary module includes an optical signal source for generating an optical signal and the no electrical communication device includes one of a transparent window and a port, and herein a communication provided by the non-electrical communication device, including the activation of the secondary module, is via the optical signal.

5. An implantable device as in claim 1, wherein the primary module includes at least one electrical circuit and the failsafe mode is effectuated by opening the at least one electrical circuit, so as to prevent an externally-applied electrical current from damaging the at least one electrical circuit.

6. An implantable device as in claim 1, wherein the at least one physiologic function is a cardiac assist function, and wherein the implantable device is a cardiac assist device.

7. An implantable device as in claim 6, wherein the implantable device is at least one of a pacemaker and a defibrillator.

8. An implantable device as in claim 6, wherein the shielding is one of a non-magnetic metal, a carbon, a carbon composite, and a combination thereof.

9. An implantable device as in claim 6, wherein the primary module includes an optical signal source for generating an optical signal and the non-electrical communication device for at least uni-directional communication is one of a transparent window and a port, and wherein a communication provided by the non-electrical commination device, including the activation of the secondary module, is via the optical signal.

10. An implantable device as in claim 6, wherein the primary module includes at least one electrical circuit and the failsafe mode is effectuated opening the at least one electrical circuit, so as to prevent an externally-applied electrical current from damaging the at least one electrical circuit.

* * * * *